US011099180B2

(12) United States Patent
Bollhagen et al.

(10) Patent No.: US 11,099,180 B2
(45) Date of Patent: Aug. 24, 2021

(54) IMMUNOASSAY USING AT LEAST TWO PEGYLATED ANALYTE-SPECIFIC BINDING AGENTS

(71) Applicant: Roche Diagnostics Operations, Inc., Indianapolis, IN (US)

(72) Inventors: Ralf Bollhagen, Penzberg (DE); Barbara Upmeier, Iffeldorf (DE); Werner Naser, Penzberg (DE); Toralf Zarnt, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 30 days.

(21) Appl. No.: 16/528,710

(22) Filed: Aug. 1, 2019

(65) Prior Publication Data

US 2019/0346432 A1 Nov. 14, 2019

Related U.S. Application Data

(63) Continuation of application No. PCT/EP2018/052343, filed on Jan. 31, 2018.

(30) Foreign Application Priority Data

Feb. 2, 2017 (EP) ..................................... 17154294

(51) Int. Cl.
*G01N 33/53* (2006.01)
*G01N 33/543* (2006.01)
*G01N 33/576* (2006.01)

(52) U.S. Cl.
CPC ... *G01N 33/54313* (2013.01); *G01N 33/5767* (2013.01); *G01N 2333/186* (2013.01)

(58) Field of Classification Search
CPC ......... G01N 33/54313; G01N 33/5767; G01N 2333/186
See application file for complete search history.

(56) References Cited

U.S. PATENT DOCUMENTS

| | | | |
|---|---|---|---|
| 4,275,149 A | 6/1981 | Litman et al. |
| 4,318,980 A | 3/1982 | Boguslaski et al. |
| 4,737,456 A | 4/1988 | Weng et al. |
| 4,816,567 A | 3/1989 | Cabilly et al. |
| 5,221,605 A | 6/1993 | Bard et al. |
| 5,521,319 A | 5/1996 | Huber et al. |
| 5,545,806 A | 8/1996 | Lonberg et al. |
| 5,545,807 A | 8/1996 | Surani et al. |
| 5,569,825 A | 10/1996 | Lonberg et al. |
| 5,591,581 A | 1/1997 | Massey et al. |
| 5,597,910 A | 1/1997 | Gudibande et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,679,519 A | 10/1997 | Oprandy |
| 6,075,181 A | 6/2000 | Kucherlapati et al. |
| 6,150,584 A | 11/2000 | Kucherlapati et al. |
| 6,391,571 B1 | 5/2002 | Kopetzki et al. |
| 6,982,321 B2 | 1/2006 | Winter |
| 7,087,409 B2 | 8/2006 | Barbas, III et al. |
| 2009/0291892 A1 | 11/2009 | Scholz et al. |

FOREIGN PATENT DOCUMENTS

| | | | |
|---|---|---|---|
| DE | 3640412 A1 | 6/1988 | |
| EP | 0404097 A2 | 12/1990 | |
| EP | 1308507 A2 | 5/2003 | |
| EP | 0967484 B1 | 5/2007 | |
| EP | 2541250 A1 * | 1/2013 | ....... G01N 33/54333 |
| WO | 1987/006706 A1 | 11/1987 | |
| WO | 1990/005296 A1 | 5/1990 | |
| WO | 1990/005301 A1 | 5/1990 | |
| WO | 1991/010741 A1 | 7/1991 | |
| WO | 1992/014139 A1 | 8/1992 | |
| WO | 1993/001161 A1 | 1/1993 | |
| WO | 1995/008644 A1 | 3/1995 | |
| WO | 1995/025882 A1 | 9/1995 | |
| WO | 1996/006946 A1 | 3/1996 | |
| WO | 1996/024690 A1 | 8/1996 | |

(Continued)

OTHER PUBLICATIONS

Boerner, Paula et al., Production of Antigen-Specific Human Monoclonal Antibodies from in Vitro-Primed Human Splenocytes, The Journal of Immunology, 1991, pp. 86-95, vol. 147.

Boulant, Steeve et al., Hepatitis C Virus Core Protein Is a Dimeric Alpha-Helical Protein Exhibiting Membrane Protein Features, Journal of Virology, 2005, pp. 11353-11365, vol. 79, No. 17.

Briggs, Mark S. J. et al., Synthesis of functionalised fluorescent dyes and their coupling to amines and amino acids, Journal of the American Chemical Society, Perkin Trans., Jan. 1997, pp. 1051-1058.

Brüggemann, Marianne et al., Comparison of the Effector Functions of Human Immunoglobulins Using a Matched Set of Chimeric Antibodies, Journal of Experimental Medicine, 1987, pp. 1351-1361, vol. 166.

Chen, Yiyan and Baker, Gregory L., Synthesis and Properties of ABA Amphiphiles, The Journal of Organic Chemistry, 1999, pp. 6870-6873, vol. 64.

(Continued)

*Primary Examiner* — Stacy B Chen
(74) *Attorney, Agent, or Firm* — Stinson LLP

(57) ABSTRACT

The disclosure concerns a method and kits for measurement of an analyte in a microparticle-based analyte-specific binding assay. In the assay, the microparticles are coated with the first partner of a binding pair, mixing the coated microparticles and at least two analyte-specific binding agents, each conjugated to the second partner of the binding pair, and a sample suspected of containing the analyte. The second partner of the binding pair is bound to each of the analyte-specific binding agents via a linker comprising from 12 to 30 ethylene glycol units (PEG 12 to 30), thereby binding the analyte via the conjugated analyte-specific binding agents to the coated microparticles. The method also entails separating the microparticles having the analyte bound via the binding pair and the analyte-specific binding agent from the mixture and measuring the analyte bound to the microparticles.

15 Claims, No Drawings

Specification includes a Sequence Listing.

(56) References Cited

FOREIGN PATENT DOCUMENTS

| | | |
|---|---|---|
| WO | 1996/033411 A1 | 10/1996 |
| WO | 1996/033735 A1 | 10/1996 |
| WO | 1996/034096 A1 | 10/1996 |
| WO | 1996/035812 A1 | 11/1996 |
| WO | 1996/039534 A1 | 12/1996 |
| WO | 1996/040978 A1 | 12/1996 |
| WO | 1996/041175 A1 | 12/1996 |
| WO | 1997/033176 A1 | 9/1997 |
| WO | 1998/012539 A1 | 3/1998 |
| WO | 1998/024893 A2 | 6/1998 |
| WO | 2003/000878 A2 | 1/2003 |
| WO | 2012/028697 A1 | 3/2012 |
| WO | 2013/001447 A1 | 1/2013 |
| WO | 2013/107633 A1 | 7/2013 |
| WO | 2016/091755 A1 | 6/2016 |
| WO | 2017/029346 A1 | 2/2017 |

OTHER PUBLICATIONS

Choo, Q.-L. et al., Genetic organization and diversity of the hepatitis C virus, Proceedings of the National Academy of Sciences USA, 1991, pp. 2451-2455, vol. 88.

Chothia, Cyrus and Lesk, Arthur M., Canonical Structures for the Hypervariable Regions of Immunoglobulins, Journal of Molecular Biology, 1987, pp. 901-917, vol. 196.

Clackson, Tim et al., Making antibody fragments using phage display libraries, Nature, 1991, pp. 624-628, vol. 352.

Cole, S .P. C. et al., The EBV-Hybridoma Technique and Its Application to Human Lung Cancer, Monoclonal Antibodies and Cancer Therapy, 1985, pp. 77-96.

De León-Rodriquez, Luis M. et al., Solid-Phase Synthesis of DOTA-Peptides, Chemistry—A European Journal, 2004, pp. 1149-1155, vol. 10.

Fellouse, Frederic A. et al., Synthetic antibodies from a four-amino-acid code: A dominant role for tyrosine in antigen recognition, Proceedings of the National Academy of Sciences USA, 2004, pp. 12467-12472, vol. 101, No. 34.

Fishwild, Dianne M. et al., High-avidity human IgGκ monoclonal antibodies from a novel strain of minilocus transgenic mice, Nature Biotechnology, 1996, pp. 845-851, vol. 14.

Hamers-Caseterman, C. et al., Naturally occurring antibodies devoid of light chains, Nature, 1993, pp. 446-448, vol. 363.

Harris, W. J., Therapeutic Monoclonals, Biochemical Society Transactions, 1995, pp. 1035-1038, vol. 23.

Holliger, Philipp et al., "Diabodies": Small bivalent and bispecific antibody fragments, Proceedings of the National Academy of Sciences USA, 1993, pp. 6444-6448, vol. 90.

Hongo, Jo-Anne S. et al., Development and Characterization of Murine Monoclonal Antibodies to the Latency-Associated Peptide of Transforming Growth Factor β1, Hybridoma, 1995, pp. 253-260, vol. 14, No. 3.

Hoogenboom, Hennie R. and Winter, Greg, By-passing Immunisation Human Antibodies from Synthetic Repertoires of Germline VH Gene Segments Rearranged in Vitro, Journal of Molecular Biology, 1992, pp. 381-388, vol. 227.

Hudson, Peter J. and Souriau, Christelle, Engineered antibodies, Nature Medicine, 2003, pp. 129-134, vol. 9, No. 1.

Hurle, Mark R. and Gross, Mitchell, Protein engineering techniques for antibody humanization, Current Opinion in Biotechnology, 1994, pp. 428-433, vol. 5.

International Search Report dated Mar. 7, 2018, in Application No. PCT/EP2018/052343, 2 pp.

Jakobovits, Aya et al., Analysis of homozygous mutant chimeric mice: Deletion of the immunoglobulin heavy-chain joining region blocks B-cell development and antibody production, Proceedings of the National Academy of Sciences USA, 1993, pp. 2551-2555, vol. 90.

Jakobovits, Aya et al., Germ-line transmission and expression of a human-derived yeast artificial chromosome, Nature, 1993, pp. 255-258, vol. 362.

Johnson, George and Wu, Tai Te, The Kabat Database and a Bioinformatics Example, Methods in Molecular Biology, 2003, 15 pp., vol. 248: Antibody Engineering: Methods and Protocols, Human Press,, Totowa, New Jersey.

Jones, Peter T. et al., Replacing the complementarity-determining regions in a human antibody with those from a mouse, Nature, 1986, pp. 522-525, vol. 321.

Knight, Andrew W. and Greenway, Gillian M., Occurrence, Mechanisms and Analytical Applications of Electrogenerated Chemiluminescence A Review, Analyst, 1994, pp. 879-890, vol. 119.

Köhler, G. and Milstein, C., Continuous cultures of fused cells secreting antibody of predefined specificity, Nature, 1975, pp. 495-497, vol. 256.

Lee, Chingwei V. et al., Bivalent antibody phage display mimics natural immunoglobulin, Journal of Immunological Methods, 2004, pp. 119-132, vol. 284.

Lee, Chingwei V. et al., High-affinity Human Antibodies from Phage-displayed Synthetic Fab Libraries with a Single Framework Scaffold, Journal of Molecular Biology, 2004, pp. 1073-1093, vol. 340.

Lewis, Michael R. et al., An Improved Method for Conjugating Monoclonal Antibodies with N-Hydroxysulfosuccinimidyl DOTA, Bioconjugate Chemistry, 2001, pp. 320-324, vol. 12.

Li, Jian et al., Human antibodies for immunotherapy development generated via a human B cell hybridoma technology, Proceedings of the National Academy of Sciences USA, 2006, pp. 3557-3562, vol. 103, No. 10.

Li, Lin et al., Vinyl Sulfone Bifunctional Derivatives of DOTA Allow Sulfhydryl- or Amino-Directed Coupling to Antibodies. Conjugates Retain Immunoreactivity and Have Similar Biodistributions, Bioconjugate Chemistry, 2002, pp. 110-115, vol. 13.

Lonberg, Nils et al., Antigen-specific human antibodies from mice comprising four distinct genetic modifications, Nature, 1994, pp. 856-859, vol. 368.

Lonberg, Noles and Huszar, Dennis, Human Antibodies from Transgenic Mice, International Reviews of Immunology, 1995, pp. 65-93, vol. 13.

Marks, James D. et al., By-passing Immunization Human Antibodies from V-gene Libraries Displayed on Phage, Journal of Molecular Biology, 1991, pp. 581-597, vol. 222.

Marks, James D. et al., By-Passing Immunization: Building High Affinity Human Antibodies by Chain Shuffling, Nature Bio/Technology, 1992, pp. 779-783, vol. 10.

Messina, Jane P. et al., Global Distribution and Prevalence of Hepatitis C Virus Genotypes, Hepatology, 2015, pp. 77-87, vol. 61.

Mier, Walter et al., Conjugation of DOTA Using Isolated Phenolic Active Esters: The Labeling and Biodistribution of Albumin as Blood Pool Marker, Bioconjugate Chemistry, 2005, pp. 237-240, vol. 16.

Morrison, Sherie L. et al., Chimeric human antibody molecules: Mouse antigen-binding domains with human constant region domains, Proceedings of the National Academy of Sciences USA, 1984, pp. 6851-6855, vol. 81.

Morrison, Sherie L., Success in specification, Nature, 1994, pp. 812-813, vol. 368.

Neuberger, Michael, Generating high-avidity human Mabs in mice, Nature Biotechnology, 1996, p. 826, vol. 14.

O'Sullivan, M. J. and Marks, V., Methods for the Preparation of Enzyme-Antibody Conjugates for Use in Enzyme Immunoassay, Methods in Enzymology, 1981, pp. 147-166, vol. 73.

Presta, Leonard G., Antibody engineering, Current Opinion in Structural Biology, 1992, pp. 593-596, vol. 2.

Rashidian, Mohammad et al., Enzymatic Labeling of Proteins: Techniques and Approaches, Bioconjugate Chemistry, 2013, pp. 1277-1294, vol. 24.

Riechmann, Lutz et al., Reshaping human antibodies for therapy, Nature, 1988, pp. 323-327, vol. 332.

(56) References Cited

OTHER PUBLICATIONS

Seitz, Oliver and Kunz, Horst, Hycron, An Allylic Anchor for High-Efficiency Solid Phase Synthesis of Protected Peptides and Glycopeptides, The Journal of Organic Chemistry, 1997, pp. 813-826, vol. 62.

Sheriff, Steven and Constantine, Keith L., Redefining the minimal antigen-binding fragment, Nature Structural Biology, 1996, pp. 733-736, vol. 3, No. 9.

Sidhu, Sachdev S. et al., Phage-displayed Antibody Libraries of Synthetic Heavy Chain Complementarity Determining Regions, Journal of Molecular Biology, 2004, pp. 299-310, vol. 338.

Van Dijk, M. A. et al., Human antibodies as next generation therapeutics, Current Opinion in Chemical Biology, 2001, pp. 368-374, vol. 5.

Vaswani, Surender K. and Hamilton, Robert G., Humanized antibodies as potential therapeutic drugs, Annals of Allergy, Asthma & Immunology, 1998, pp. 105-119, vol. 81.

Xu, John L. and Davis, Mark M., Diversity in the CDR3 Region of VH is Sufficient for Most Antibody Specificities, Immunity, 2000, pp. 37-45, vol. 13.

\* cited by examiner

IMMUNOASSAY USING AT LEAST TWO PEGYLATED ANALYTE-SPECIFIC BINDING AGENTS

CROSS-REFERENCE TO RELATED APPLICATIONS

This application is a continuation of International Application No. PCT/EP2018/052343 filed Jan. 31, 2018, which claims priority to European Application No. 17154294.7 filed Feb. 2, 2017, the disclosures of which are hereby incorporated by reference in their entirety.

The present invention relates to a method for measurement of an analyte in a microparticle-based analyte-specific binding assay, wherein said microparticles are coated with the first partner of a binding pair, the method comprising mixing the coated microparticles, at least two analyte-specific binding agents, bound to the second partner of the binding pair, and a sample suspected of comprising or comprising the analyte, wherein said second partner of the binding pair is bound to said analyte-specific binding agents via a linker comprising from 12 to 30 ethylene glycol units (PEG 12 to 30), thereby binding the analyte via the analyte-specific binding agents to the coated microparticles, separating the microparticles comprising the analyte bound via the binding pair and the analyte-specific binding agents from the mixture and measuring the analyte bound to the microparticles. In addition, the invention relates to detecting several variants of an analyte applying the above concept, in particular the detection of viral antigens.

BACKGROUND OF THE INVENTION

Numerous methods and systems have been developed for the detection and quantitation of analytes of interest in biochemical and biological samples. Methods and systems which are capable of measuring trace amounts of microorganisms, pharmaceuticals, hormones, viruses, antibodies, nucleic acids and other proteins are of great value to researchers and clinicians.

Many assay methods make use of an analyte-specific binding agent to capture a specific target molecule of interest from a sample and allow for determination of the target molecule.

A substantial body of art has been developed based upon binding reactions, e.g., antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the analyte-specific binding agents.

Assays sensitivity is largely limited by non-specific binding phenomena. Thus the main difficulty is to conceive an assay technology that is very sensitive and that at the same time does not intrinsically suffer from a high background signal, e.g. caused by the sample fluid that is probed. Non-specific binding typically leads to an increased background signal, to an inaccurate detection and to a higher (worse) detection limit. In particular, nonspecific binding is even more challenging when complex biological matrices such as human plasma or serum samples are used as sample fluids.

In recent years, more accurate and sensitive assays have been developed, which are based on the use of (e.g. superparamagnetic) microparticles. Especially in such particle-based assays, important contributions to nonspecific signals come from particle-particle interactions and/or from particle-surface interactions.

U.S. Pat. No. 5,212,063 discloses a process for the detection of analytes in body fluids containing free biotin by immunoassay which make use of biotin conjugates. The document mentions polymer microparticles consisting of a core and containing a polymer which has a plurality of binding sites for biotin and, as a covering, at least one layer of protein.

WO 2013/001447 describes a precoated microparticle having a coating comprising a shell structure, wherein said shell structure comprises a first layer comprising one or more affinity molecules (i.e. an analyte-specific binding agent) and further a second layer, which is coupled to the first layer, and wherein said first and second layer comprises non-affine spacer molecules forming a mesh, wherein said one or more affinity molecules are embedded within the coating structure and wherein said mesh generates a steric hindrance for non-specific molecules. Using such especially treated/coated microparticles the background caused by non-specific binding could be reduced. However, even the most advanced assays still exhibit significant levels of non-specific binding impairing either the lower limit of detection (LOD) or the measuring range or both. Test developers often have to compromise between assay sensitivity, measuring range and assay specificity. At the same time the tests need to be rapid, sensitive, quantitative accurate and even cost-effective. Moreover the platform on which the test is to be performed needs to be easy to use and reliable.

Another challenge for in vitro diagnostic methods is the fact that an analyte exists in more than one form or variation. As certain analytes appear as different variants like different mutants, isoforms, different genotypes and/or different serotypes the in vitro diagnostic assay design often requires more than one analyte-specific binding agent in order to guarantee a sufficient assay sensitivity. Usually one capture component has got a higher affinity towards a certain variant of the analyte than the other one or more capture components. In particular in the infectious disease diagnostics environment usually all variants of an analyte have to be detected to fulfill the required degree of sensitivity.

In addition, there is always a desire to improve assays by increasing ratio of signal to background noise and, therefore, the sensitivity of the assay. Increasing the signal of an assay also has several instrumental advantages including: i) less sensitive (and less expensive) detection systems are required; ii) smaller amounts of valuable samples are required; iii) instrumentation may be miniaturized so as to allow for instruments that are smaller and/or devices that run many assays concurrently in a small area.

However, especially in particle-based assays, important contributions to nonspecific signals come from particle-particle interactions and particle-surface interactions.

There is thus a need to design novel structures and methods for improved particle-based assay methods, in particular for assay methods detecting an analyte that appears in different variations. There is a strong need to avoid non-specific binding to and clustering of microparticles, which is a limiting factor in a huge number of detection assays.

It has now surprisingly been found that linker molecules comprising between 12 and 30 polyethylene glycol units—bound on the one hand to one member of a binding pair and on the other hand to an analyte-specific binding agent—can be used with great advantage in a microparticle-based binding assay, wherein the microparticles are coated with the other member of the binding pair. In addition, it has unexpectedly been found that these compounds—compared to the short linker structures described in prior art—provide a superior assay sensitivity when at least two analyte-specific binding agents are used that are bound to the above linker molecules thereby providing a reliable sensitive detection of analytes in particular in the infectious diseases area.

WO 2017/029346, published after filing of application no. EP 17154294.7, priority of which is claimed for the present patent application, discloses a method for detecting an analyte in a microparticle-based assay using linker molecules comprising between 12 and 30 polyethylene glycol units that connect an analyte-specific binding agent to a partner of a binding pair (such as e.g. biotin). The microparticles are coated with the other partner of the binding pair, such as e.g. streptavidin. WO 2017/029346 describes the general concept of applying these PEG linkers but does not elaborate on the number of specific binding agents that are required to detect analytes that exist in more than one form or variation with high sensitivity.

SUMMARY OF THE INVENTION

Disclosed is a method for measurement of an analyte in a microparticle-based analyte-specific binding assay, wherein said microparticles are coated with the first partner of a binding pair, the method comprising a) mixing the coated microparticles, at least two analyte-specific binding agents, wherein each of said analyte-specific binding agents is bound to the second partner of the binding pair, and a sample suspected of comprising or comprising the analyte, wherein said second partner of the binding pair is bound to said analyte-specific binding agents via a linker comprising from 12 to 30 ethylene glycol units (PEG 12 to 30), thereby binding the analyte via the analyte-specific binding agents to the coated microparticles, b) separating the microparticles comprising the analyte bound via the binding pair and the analyte-specific binding agents from the mixture and c) measuring the analyte bound to the microparticles. Disclosed is also said method for measurement of an analyte that appears in several variants.

Also disclosed is a kit comprising in separate containers or in separated compartments of a single container unit at least microparticles coated with the first member of a binding pair and at least two analyte-specific binding agents bound to the second member of this binding pair, wherein said second member of said binding pair is bound to said analyte-specific binding agents via a linker comprising from 12 to 30 ethylene glycol units (PEG 12 to 30).

DETAILED DISCLOSURE OF THE INVENTION

In one embodiment the present disclosure relates to a method for measurement of an analyte in a microparticle-based analyte-specific binding assay, wherein said microparticles are coated with the first partner of a binding pair, the method comprising a) mixing the coated microparticles, at least two analyte-specific binding agents bound to the second partner of the binding pair, and a sample suspected of comprising or comprising the analyte, wherein said second partner of the binding pair is bound to said analyte-specific binding agents via a linker comprising from 12 to 30 ethylene glycol units (PEG 12 to 30), thereby binding the analyte via the analyte-specific binding agents to the coated microparticles, b) separating the microparticles comprising the analyte bound via the binding pair and the analyte-specific binding agents from the mixture and c) measuring the analyte bound to the microparticles.

Particle-based analyte-specific binding assays are widely used in e.g. certain nephelometric assays, certain latex agglutination assays and many sensitive sandwich type assays employing a broad variety of labeling or detection techniques.

A "particle" as used herein means a small, localized object to which can be ascribed a physical property such as volume, mass or average size. Microparticles may accordingly be of a symmetrical, globular, essentially globular or spherical shape, or be of an irregular, asymmetric shape or form. The size of a particle envisaged by the present invention may vary. In one embodiment used are of globular shape, e.g. microparticles with a diameter in the nanometer and micrometer range. In one embodiment the microparticles used in a method according to the present disclosure have a diameter of 50 nanometers to 20 micrometers. In a further embodiment the microparticles have a diameter of between 100 nm and 10 µm. In one embodiment the microparticles used in a method according to the present disclosure have a diameter of 200 nm to 5 µm or from 750 nm to 5 µm.

Microparticles as defined herein above may comprise or consist of any suitable material known to the person skilled in the art, e.g. they may comprise or consist of or essentially consist of inorganic or organic material. Typically, they may comprise or consist of or essentially consist of metal or an alloy of metals, or an organic material, or comprise or consist of or essentially consist of carbohydrate elements. Examples of envisaged material for microparticles include agarose, polystyrene, latex, polyvinyl alcohol, silica and ferromagnetic metals, alloys or composition materials. In one embodiment the microparticles are magnetic or ferromagnetic metals, alloys or compositions. In further embodiments, the material may have specific properties and e.g. be hydrophobic, or hydrophilic. Such microparticles typically are dispersed in aqueous solutions and retain a small negative surface charge keeping the microparticles separated and avoiding non-specific clustering.

In one embodiment of the present invention, the microparticles are paramagnetic microparticles and the separation of such particles in the measurement method according to the present disclosure is facilitated by magnetic forces. Magnetic forces are applied to pull the paramagnetic or magnetic particles out of the solution/suspension and to retain them as desired while liquid of the solution/suspension can be removed and the particles can e.g. be washed.

The microparticles used in a method according to the present invention are coated with the first member of a specific binding pair.

A "binding pair" as used herein consists of two partners binding to each other with high affinity, i.e. with one nanomolar affinity or better. Embodiments for binding pairs are for example the binding pairs consisting of receptor and ligand, hapten and anti-hapten antibody, and binding pairs based on naturally occurring high affinity binding pairs.

One example of a receptor-ligand binding pair is a pair consisting of a steroid hormone receptor and the corresponding steroid hormone.

One type of a binding pair which is suitable for the method according to the present invention is a hapten and anti-hapten antibody binding pair. A hapten is an organic molecule with a molecular weight of 100 to 2000 Dalton, preferably of 150 to 1000 Dalton. Such small molecule can be rendered immunogenic by coupling it to a carrier molecule and anti-hapten antibodies can be generated according to standard procedures. The hapten may be selected from the group comprising sterols, bile acids, sexual hormones, corticoids, cardenolides, cardenolide-glycosides, bufadienolides, steroid-sapogenines and steroid alkaloids, cardenolides and cardenolide-glycosides. Representatives of these substance classes are digoxigenin, digitoxigenin, gitoxigenin, strophanthidin, digoxin, digitoxin, ditoxin, and strophanthin. Another suitable hapten is for example fluorescein.

Examples of binding pairs based on naturally occurring high affinity binding pairs are biotin or biotin analogues such as aminobiotin, iminobiotin or desthiobiotin and avidin or streptavidin as well as the FimG and DsF binding pair. The biotin-(strept)avidin binding pair is well-known in the art. The basic principles of the FimG-DsF binding pair are e.g. described in WO2012/028697.

In one embodiment binding pairs are selected from hapten and anti-hapten antibody, biotin or biotin analogues such as aminobiotin, iminobiotin or desthiobiotin and avidin or streptavidin, FimG and DsF, and receptor and ligand.

In one embodiment binding pairs are selected from hapten and anti-hapten antibody and biotin or biotin analogues such as aminobiotin, iminobiotin or desthiobiotin/avidin or streptavidin, FimG and DsF.

In one embodiment the binding pair is biotin (or biotin analogues such as aminobiotin, iminobiotin or desthiobiotin) and avidin or streptavidin.

In one embodiment the binding pair consists of biotin and streptavidin.

In one embodiment the binding pair according to the present invention consists of a first partner of such binding pair having a molecular weight of 10 kD or more and of a second pair of such binding pair having a molecular weight of 1 kD or less. As indicated above, the first partner of a binding pair, in one embodiment having a molecular weight of 10 kD or more, is bound (coated) to the microparticles used in a method according to the present disclosure.

In one embodiment in the microparticle-based method according to the present disclosure said first partner of the binding pair is selected from avidin and/or streptavidin, and FimG, respectively, and wherein said second partner of the binding pair is selected from biotin or biotin analogues such as aminobiotin, iminobiotin or desthiobiotin and DsF, respectively.

In one embodiment in the microparticle-based method according to the present disclosure said first partner of the binding pair is avidin and/or streptavidin and wherein said second partner of the binding pair is biotin.

The microparticles used in a method according to the present invention are "coated" with the first partner of a binding pair. Such coating is performed according to state of the art procedures. The first partner of the binding pair can be bound to the surface of the particle by adsorption, by covalent binding or a combination of both methods. The microparticles optionally can be further incubated, e.g. with proteins, like bovine serum albumin, to reduce non-specific binding of other assay components. The skilled artisan is fully aware of the methods used for such optional blocking of non-specific binding. In line with the terminology used in the art, such coated and blocked microparticles also are simply referred to as coated microparticles.

The molecules of the first partner of the binding pair are present on the microparticle in close proximity providing for many nearby binding sites for the second partner of this binding pair. For most practical/routine applications the first partner of the binding pair is coated to the microparticles at saturation concentration, resulting in an optimal coating density. As the skilled artisan appreciates, the coating density, if desired could be reduced by using sub-optimal concentrations of the first partner of a binding pair. In case a sub-optimal concentration of the first partner of a binding pair would be used for coating the person skilled in the art would choose the average coating density to match the linker length used for binding the analyte-specific binding agent to the second partner of the binding pair. In general terms: The average distance between the molecules of a first partner of a binding pair on a coated microparticle will be at most twice the length of the linker used for binding the analyte-specific binding agent to the second partner of the binding pair. The distance hereby is from the center of one molecule to the center of another molecule. As an example: The average length of a polyethylene glycol unit is about 0.38 nm. Thus a linker with 12 PEG-units has about 4.5 nm in length. In order to allow the molecules of the second partner of a binding pair to bind to the first partners of said binding pair on the same microparticle the average distance between the molecules of the first partner of the binding pair on the particle would be 9 nm or less. In one embodiment the average distance of the molecules of the first partner of a binding pair is 9 nm or less. In one embodiment the average distance of the molecules of the first partner of a binding pair is 9 nm or 8 nm, respectively. In one embodiment microparticles are used which have been coated at saturation concentration of/with the first partner of a binding pair.

An "analyte" or "analyte of interest" or "target molecule" can be any molecule which can be bound by an analyte-specific binding agent. In one embodiment, an analyte within the context of the present invention is a nucleic acid (DNA or RNA) molecule, a peptide, a protein, a drug molecule, a hormone or a vitamin. In one embodiment, an analyte within the context of the present invention is a peptide, a protein, a drug molecule, a hormone or a vitamin.

In another embodiment, an analyte comprises several variants, in an embodiment different genotypes, isoenzymes, isoforms, serotypes or mutants of an analyte. In an embodiment, an analyte is an antigen of an infectious agent. Examples of infectious agents are viruses, bacteria and protozoic pathogens that infect humans. In an embodiment, an analyte is a viral antigen, in an embodiment a hepatitis virus antigen or a human retroviral antigen. In an embodiment, an analyte is a hepatitis C virus or hepatitis B virus or HIV antigen.

In yet another embodiment, an analyte is hepatitis C virus core, NS3 or NS4 antigen. In an embodiment, an analyte is an antigen present within SEQ ID NO:1 which shows the complete amino acid sequence of hepatitis C virus core antigen, genotype 1a. In an embodiment, an analyte has the complete amino acid sequence of SEQ ID NO:1 which shows the amino acid sequence of Hepatitis C virus genotype 1a (isolate 1), also accessible via UniProt database, accession no. P26664. In an embodiment an analyte is a partial sequence of SEQ ID NO:1, in an embodiment a partial sequence of at least consecutive 10 amino acids, in an embodiment of at least 20 consecutive amino acids of SEQ ID NO:1. In yet another embodiment, an analyte is a variant of the antigen shown in SEQ ID NO:1 Variants and genotypes of HCV core have been described in literature, see e.g. Choo et al., PNAS 88 (1991), p. 2451-2455. In another embodiment an analyte has the complete amino acid sequence of one of HCV genotypes 1-7 core protein or a partial sequence thereof of at least 20 amino acid residues. HCV genotypes, their prevalence and global distribution have been well-described in the art and summarized e.g. by Messina et al., Hepatology 2015 61(1), p. 77-87.

SEQ ID NO:1

| | | |
|---|---|---|
| MSTNPKPQKK | NKRNTNRRPQ | DVKFPGGGQI |
| VGGVYLLPRR | GPRLGVRATR | KTSERSQPRG |
| RRQPIPKARR | PEGRTWAQPG | YPWPLYGNEG |
| CGWAGWLLSP | RGSRPSWGPT | DPRRRSRNLG |
| KVIDTLTCGF | ADLMGYIPLV | GAPLGGAARA |
| LAHGVRVLED | GVNYATGNLP | GCSFSIFLLA |
| LLSCLTVPAS A | | |

In an embodiment an analyte is a variant of SEQ ID NO:1 wherein said variant comprises a partial sequence of at least 10, in an embodiment of at least 20 consecutive amino acids of SEQ ID NO:1 and has 90% sequence identity over said partial sequence. For example, in a partial sequence comprising 50 amino acids, 45 amino acids are identical to SEQ ID NO:1 and 5 have been substituted by other amino acids. In an embodiment substituted amino acid residues have been replaced by conservative exchanges, for illustration e.g. replacing valine by isoleucine or replacing an acidic amino acid by another acidic amino acid (glutamic acid/aspartic acid).

Liquid samples can be used in a method for specific in vitro-detection of an analyte in a method according to the present disclosure. The sample may be known to comprise the analyte or it may be suspected of comprising the analyte. In one embodiment a sample for in vitro diagnosis used in a method according to the present disclosure is a body fluid selected from whole blood, blood serum, blood plasma, liquor, urine or saliva. In one embodiment the sample suspected of comprising or comprising the analyte is serum, plasma or liquor. In one embodiment the sample suspected of comprising or comprising the analyte is serum or plasma.

The method for measurement of an analyte according to the present disclosure makes use of at least two analyte-specific binding agents. The term "analyte-specific binding agent" refers to a molecule specifically binding to the analyte of interest.

The term "at least two analyte-specific binding agents" refers to at least two molecules each specifically binding to the analyte of interest but having different affinities to the analyte. In an embodiment, said at least two analyte-specific binding agents can be two different antibodies, each of which recognizes a different epitope on an analyte. In an embodiment, said epitopes are distinct epitopes, i.e. their amino acid sequences or their recognized binding sites do not overlap so that the at least two antibodies do not compete in binding to their respective epitope so that they can be attached or bound to the analyte in parallel, at the same time. In case an antibody is the analyte of interest the at least two analyte-specific binding agents are each antigens based on a polypeptide. In that case the antigens differ in their polypeptide sequence to such a degree that the analyte antibody binds to both of the at least two antigens (acting as analyte-specific binding agents) but with different affinity. The definitions for an "analyte-specific binding agent" provided further below apply mutatis mutandis to each of the "at least two analyte-specific binding agents".

An analyte-specific binding agent in the sense of the present disclosure typically comprises binding or capture molecules capable of binding to an analyte (other terms analyte of interest; target molecule). In one embodiment the analyte-specific binding agent has at least an affinity of $10^7$ l/mol for its corresponding target molecule, i.e. the analyte. The analyte-specific binding agent in other embodiments has an affinity of $10^8$ l/mol or even of $10^9$ l/mol for its target molecule. In an embodiment, the affinity of an analyte-specific binding agent to its target molecule is at least $10^{10}$ l/mol. As the skilled artisan will appreciate the term specific is used to indicate that other biomolecules present in the sample do not significantly bind to the binding agent specific for the analyte. In some embodiments, the level of binding to a biomolecule other than the target molecule results in a binding affinity which is only 10%, more preferably only 5% of the affinity of the target molecule or less. In one embodiment no binding affinity to other molecules than to the analyte is measurable. In one embodiment the analyte-specific binding agent will fulfill both the above minimum criteria for affinity as well as for specificity.

In one embodiment the analyte-specific binding agent is selected from the group consisting of aptamers, peptide aptamers, proteins, oligonucleotides, and molecular imprinted polymers.

An "aptamer" as used within the context of an analyte-specific binding agent may be a short nucleic acid molecule, e.g. an RNA, DNA, PNA, CNA, HNA, LNA or ANA molecule or any other suitable nucleic acid format known to the person skilled in the art, being capable of binding an analyte.

Peptide aptamers are aptamers which are able to specifically bind to (a) protein(s), polypeptide(s) or peptide(s) comprising a specific amino acid sequence. Typically, a peptide aptamer has a peptide loop, comprising for example 10 to 20 amino acids. In the context of the present disclosure a peptide aptamer may in specific embodiments be attached at one or both ends to a scaffold structure. The scaffold structure may be any molecule, preferably a protein, e.g. a protein, which has good solubility properties. Suitable scaffold molecules would be known to the person skilled in the art. Example of suitable scaffold molecules are based on bacterial protein thioredoxin-A, and FkpA- or SlyD-chaperones, respectively. The aptamer peptide loop may preferably be inserted within a reducing active site of the scaffold molecule. Alternatively, staphylococcal protein A and domains thereof and derivatives of these domains, such as protein Z or lipocalins may be used as peptide aptamers.

Nucleic acid or peptide aptamers may be generated according to any suitable method known to the person skilled in the art, e.g. via PCR or molecular synthesis approaches or yeast two-hybrid approaches.

A "peptide" as used within the context of an analyte-specific binding agent may comprise or alliteratively consist of a stretch of 2 to 49 amino acids, amino acid derivatives or a mixture thereof. The peptide may be linear, branched, circular or a mixture thereof. A peptidic analyte-specific binding agent may also be attached to a scaffold structure as defined herein above.

A "polypeptide" or "protein" as used within the context of an analyte-specific binding agent may comprise or alternatively consist of a stretch of more than about 50 amino acids, amino acid derivatives or a mixture thereof. The protein may have a linear, branched, and circular form or be comprised of a mixture of these forms.

In one embodiment the analyte-specific binding agent is a polypeptide of at least 50 amino acids. Though in theory there is no upper limit to the polypeptide length of an analyte-specific binding agent in one embodiment will have at most 10.000 amino acids.

An "oligonucleotide" as used within the context of an analyte-specific binding agent may comprise or alternatively consist of a stretch of 10 to 120 nucleotides, or of 12 to 60, or of 15 to 40 nucleotides.

An oligonucleotide analyte-specific binding agent may be an RNA molecule or a DNA molecule, or a mixture of both.

The term "molecular imprinted polymer" as used herein refers to a polymer which was formed in the presence of a molecule that is extracted afterwards, leaving a complementary cavity (an imprint) behind. Typically, a molecular imprinted polymer shows a certain chemical affinity for the original molecule. A molecular imprinted polymer may be composed of any suitable polymeric unit known to the person skilled in the art. Techniques for their production include polymerization techniques such as bulk, precipitation, emulsion, suspension, dispersion, gelation, multi-step swelling polymerization and hierarchical imprinting methods.

An "antibody" as used in the context of an analyte-specific binding agent refers to an immunoglobulin molecule and to an immunologically active portion (fragment) of an immunoglobulin molecule, i. e. antibodies or antibody fragments that contain an antigen binding site that immunospecifically binds the analyte. The immunoglobulin molecules used in a method according to the present invention can be of any type (e. g., IgG, IgE, IgM, IgD, IgA and IgY), class (e. g., IgG1, IgG2, IgG3, IgG4, IgA1 and IgA2) or subclass of immunoglobulin molecules. Antibodies can be described or specified in terms of the epitope(s) or portion(s) of a polypeptide which they recognize or specifically bind. Specific epitopes and their interaction with antibodies would be known to the person skilled in the art.

The term "analyte-specific binding" as used in the context of an antibody refers to the immunospecific binding of an antibody to an epitope on the analyte. The concept of analyte-specific binding of an antibody via its epitope on an analyte is fully clear to the person skilled in the art.

The term "antibody" herein is used in the broadest sense and specifically covers monoclonal antibodies, polyclonal antibodies, single chain antibodies, multispecific antibodies (e.g. bispecific antibodies) formed from at least two different antibodies, and antibody fragments so long as they exhibit the desired biological activity. An antibody in the sense of the present disclosure may also be part of a larger fusion molecule, formed by covalent or non-covalent association of the antibody with one or more other proteins or peptides.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified to greater than 95% by weight of antibody, and in some embodiments, to greater than 99% as determined by SDS-PAGE under reducing or nonreducing conditions using, for example, Coomassie blue or silver stain.

Antibodies of the immunoglobulin G class usually are heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

The antibodies used in a method according to the present invention may be from any animal origin. In one embodiment the antibodies are human, murine (e. g., mouse and rat), donkey, monkey, rabbit, goat, guinea pig, camel, horse, or chicken antibodies.

Depending on the amino acid sequences of the constant domains of their heavy chains, antibodies (immunoglobulins) can be assigned to different classes. There are five major classes of human immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, β, ε, γ, and µ, respectively. The subunit structures and three-dimensional configurations of different classes of immunoglobulins are well known and described generally in, for example, Abbas et al. *Cellular and Mol. Immunology*, 4th ed. (W. B. Saunders, Co., 2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. Examples of antibody fragments include Fab, Fab', F(ab')$_2$, and Fv fragments; single-chain antibody molecules; scFv, sc(Fv)2; diabodies; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody-hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species (sc(Fv)2). It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404097; WO 1993/01161; Hudson et al., Nat. Med. 9:129-134 (2003); and Holliger et al., PNAS USA 90: 6444-6448 (1993). Triabodies and tetrabodies are also described in Hudson et al., Nat. Med. 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2$^{nd}$ ed. 1988); Haemmerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, PNAS USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., PNAS USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (e.g., U.S. Pat. No. 4,816,567 and Morrison et al., PNAS USA 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all, or substantially all, of the FRs are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is one which possesses an amino-acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227: 381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., PNAS USA, 103:3557-3562 (2006) regarding human antibodies generated via a human B-cell hybridoma technology.

The term "hypervariable region," "HVR," or "HV," when used herein refers to the regions of an antibody-variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. Immunity 13:37-45 (2000); Johnson and Wu in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993) and Sheriff et al., Nature Struct. Biol. 3:733-736 (1996).

A number of HVR delineations are in use and are encompassed herein. The HVRs that are Kabat complementarity-determining regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop Kabat | AbM | Chothia | Contact |
|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (H2), and 93-102, 94-102, or 95-102 (H3) in the VH. The variable-domain residues are numbered according to Kabat et al., supra, for each of these extended-HVR definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

In an embodiment, the at least two antigen-specific binding agents are antibodies that bind to an epitope of the analyte. An epitope is the part of an antigen that is specifically bound by an antibody. Epitopes can be either linear (contiguous or neighboring amino acids on one polypeptide chain) or conformational (three-dimensional polypeptide structure that interacts with the paratope/antigen binding site of the antibody). In an embodiment, said epitopes are distinct epitopes, i.e. their amino acid sequences or their recognized binding sites do not overlap so that the at least two antibodies do not compete in binding to their respective epitope so that they can be attached or bound to the analyte in parallel, at the same time. In an embodiment of the invention, the at least two viral antigen-specific binding agents are antibodies, one of which binds to an epitope within the amino acid positions 140 to 172, in an embodiment within amino acid positions 157-169 of SEQ ID NO:1 and one of which binds to an epitope within the amino acid positions 20 to 80, in an embodiment within the amino acid positions 65-71, in an embodiment within the amino acid positions 32-36, in an embodiment within the amino acid positions 37-46 of SEQ ID NO:1.

As disclosed herein, the second partner of the binding pair is bound to the analyte-specific binding agent via a linker comprising from 12 to 30 ethylene glycol units (PEG 12 to 30).

The term "linker" denotes a bifunctional or multifunctional moiety which can be used to conjugate (link) a first moiety with a second moiety or more moieties. Conjugates comprising a first and a second moiety bound to each other can be conveniently prepared using a linker having two reactive functionalities. In such conjugate the two moieties are bound "via" this linker. As obvious to the skilled artisan in such conjugate the functional moieties of the linker are present as part of a bond and not as an unreacted functional moiety.

We believe that the linker comprising from 12 to 30 ethylene glycol units is key to the surprising findings disclosed herein. In the prior art on microparticle-based assays for measurement of an analyte only short PEG-containing linker molecules are seriously considered. U.S. Pat. No. 5,521,319 discloses a novel reagent that proved very useful for biotinylation of biomolecules. The length of the linker is taught to be short, i.e. up to 5 units of ethylene oxide, preferably of only 1 to 3 units of ethylene oxide and most preferred of two such units. Contrary to this teaching it has now surprisingly been found that in a microparticle-based analyte-specific binding assay long linker molecules—comprising between 12 to 30 ethylene oxide units (=PEG 12 to 30)—are advantageous if used to couple a the second member of a binding pair, e.g. a biotin, to the analyte-specific agent.

An appropriate reagent for linking or coupling biotin via a PEG-linker to a target molecule is for example a reagent according to Formula I

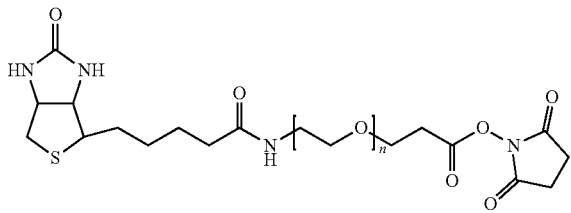

As will be appreciated (n) in Formula I relates to the number of ethylene glycol units. n preferably is from 12 to 30.

The methods of the invention may be constructed in a wide variety of formats. Such formats include formats known in the art such as e.g. sandwich assays. (see, e.g., the following references: Nonradioactive Labeling and Detection of Molecules, Kessler, C., ed., Springer-Verlag: Berlin 1992; The Immunoassay Handbook, Wild, D., ed., Stackton Press: New York 1994; Keller, G. H. and Manak, M. M. DNA Probes, 2nd Ed., MacMillan Publishers Ltd.: London, 1993; Tietz Textbook of Clinical Chemistry 2nd Edition, Burtis et al. Ed., W. B. Saunders and Co.: Philadelphia, 1994).

In a method according to the present disclosure an analyte is measured. As the person skilled in the art will readily appreciate the measuring of the analyte bound to the microparticles is usually made by measurement of a signal carried or generated by a label on an appropriate assay component and by calculating the concentration of the analyte from a standard curve for the analyte, i.e. thereby measuring the analyte. The assay component to which a label is usually attached is a further analyte-specific binding agent (sandwich-type assays). Before the label is measured, the microparticles comprising part the labeled assay component are separated from the part of the labeled assay component not bound to the microparticles.

In one embodiment the method of the present disclosure is practiced in a sandwich assay format.

A typical sandwich assay format includes mixing a microparticle coated with the first partner of a binding pair, at least two analyte-specific binding agents, each bound to the second partner of the binding pair, a sample suspected of comprising or comprising the analyte, wherein said second partner of the binding pair is bound to each of said analyte-specific binding agents via a linker comprising from 12 to 30 ethylene glycol units (PEG 12 to 30), and a further analyte-specific binding agent which is detectably labeled. As obvious to the skilled artisan these components are mixed and incubated for a period of time sufficient for binding the detectably labeled analyte-specific binding agent via the analyte, the analyte-specific binding agents (bound to) the second partner of the binding pair and the first partner of the binding pair to the microparticles. In one embodiment, a sandwich assay without washing step, such mixing/incubation is performed in a single reaction vessel. The sequence of adding and mixing the four ingredients (coated microparticles, sample, analyte-specific binding agents each bound to the second partner of the binding pair, and detectably-labeled analyte-specific binding agent, respectively) is not critical. In one embodiment, a sandwich assay with a washing step, the adding and mixing of microparticles coated with the first member of a binding pair, sample and analyte-specific binding agent bound to the second partner of the binding pair is performed in a single reaction vessel. After this first (analyte-capturing) step the microparticles to which the analyte is now bound are washed before adding the detectably-labeled analyte-specific binding agent. The sequence of adding and mixing of the first three ingredients (coated microparticles, sample and analyte-specific binding agent bound to the second partner of the binding pair, respectively) is not critical.

In a sandwich-type assay format in one embodiment the at least two analyte-specific binding agents, each bound to the second partner of the binding pair, and the detectably-labeled analyte-specific binding agent, respectively, each bind to the analyte at different and non-overlapping epitopes.

Methods for labeling of an analyte-specific binding agent or of an analyte are well-known to the person skilled in the art and abundantly described e.g. in Haugland (2003) Molecular Probes Handbook of Fluorescent Probes and Research Chemicals, Molecular Probes, Inc.; Brinkley (1992) Bioconjugate Chem. 3:2; Garman, (1997) Non-Radioactive Labeling: A Practical Approach, Academic Press, London; Means (1990) Bioconjugate Chem. 1:2; Glazer et al. Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGruyter, Berlin and New York; and Wong (1991) Chemistry of Protein Conjugation and Cross-linking, CRC Press, Boca Raton, Fla.); DeLeon-Rodriguez et al., Chem. Eur. J. 10 (2004) 1149-1155; Lewis et al., Bioconjugate Chem. 12 (2001) 320-324; Li et al., Bioconjugate Chem. 13 (2002) 110-115; Mier et al. Bioconjugate Chem. 16 (2005) 240-237.

The term detectably labeled encompasses labels that can be directly or indirectly detected.

Indirectly detectably labeled refers, e.g. to labeling with a hapten and to the detection of such haptenylated compound by an anti-hapten antibody carrying a directly detectable label or to the labeling with an enzyme and to the detection of such enzyme by its corresponding enzymatic activity resulting in the conversion of an appropriate dye substrate. Various enzyme-substrate labels are available or disclosed (see e.g. U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to polypeptides are described in O'Sullivan et al. "Methods for the Preparation of Enzyme-Antibody Conjugates for use in Enzyme Immunoassay", in Methods in Enzym. (ed. by J. Langone & I T Van Vunakis), Academic Press, New York, 73 (1981) 147-166.

Examples of enzyme-substrate combinations (U.S. Pat. Nos. 4,275,149; 4,318,980) include, for example: Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB)); alkaline phosphatase (AP) with para-nitrophenyl phosphate as chromogenic substrate; and (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

Directly detectable labels either provide a detectable signal or they interact with a second label to modify the detectable signal provided by the first or second label, e.g. to give FRET (fluorescence resonance energy transfer). Labels such as fluorescent dyes and luminescent (including chemiluminescent and electrochemiluminescent) dyes (Briggs et al. "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling. In one embodiment detectably labeled refers to a label providing or inducible to provide a detectable signal, i.e. to a fluorescent label, to a chemiluminescent label or to an electrochemiluminescent label, respectively.

In one embodiment according to the present disclosure the microparticle-based analyte-specific binding assay makes use of a chemiluminescent or an electrochemiluminescent label and a corresponding light detection system. The light produced by the label is measured and directly or indirectly indicates the presence or quantity of the analyte.

Electrochemiluminescent (ECL) assays provide a sensitive and precise measurement of the presence and concentration of an analyte of interest. Such techniques use labels or other reactants that can be induced to luminesce when electrochemically oxidized or reduced in an appropriate chemical environment. Such electrochemiluminescence is triggered by a voltage imposed on a working electrode at a particular time and in a particular manner. The light produced by the label is measured and indicates the presence or quantity of the analyte. For a fuller description of such ECL techniques, reference is made to U.S. Pat. Nos. 5,221,605, 5,591,581, 5,597,910, PCT published application WO90/05296, PCT published application WO92/14139, PCT published application WO90/05301, PCT published application WO96/24690, PCT published application US95/03190, PCT application US97/16942, PCT published application US96/06763, PCT published application WO95/08644, PCT published application WO96/06946, PCT published application WO96/33411, PCT published application WO87/06706, PCT published application WO96/39534, PCT published application WO96/41175, PCT published application WO96/40978, PCT/US97/03653 and U.S. patent application Ser. No. 08/437,348 (U.S. Pat. No. 5,679,519). Reference is also made to a 1994 review of the analytical applications of ECL by Knight, et al. (Analyst, 1994, 119: 879-890) and the references cited therein. In one embodiment the method according to the present description is practiced using an electrochemiluminescent label.

As mentioned above electrochemiluminescence is triggered by a voltage imposed on a working electrode at a particular time and in a particular manner. What is not mentioned in detail in the prior art is the fact the distribution of microparticles on the working electrode has a major impact on the quality of an assay. The more aggregates in between microparticles are present—as a rule of thumb—the lower the quality of one or more assay features. Aggregated particles often lead to a higher co-efficient of variation in between measurements, higher background signals and/or reduced assay sensitivity.

As can be easily imagined, the use of at least two analyte-specific binding agents, each bound to the second partner of the binding pair and comprising two or more molecules of the second binding partner per molecule of the analyte-specific binding agent can easily lead to aggregation of microparticles coated with (many molecules of) the first partner of the binding pair. Therefore in the prior art many attempts have been made to produce conjugates consisting of one molecule of analyte-specific binding agent and one molecule of the second partner of the binding pair. Methods appropriate for obtaining such 1:1 conjugates are e.g. described in U.S. Pat. No. 6,391,571.

One of the most important recent approaches for site-specific protein labeling, especially site-specific mono-labeling of proteins is to incorporate bioorthogonal functionalities into these proteins at specific sites via enzymatic reactions. For a recent review on "enzymatic labeling of proteins" see M. Rashidian et al., Bioconjugate Chemistry 24 (2013) 1277-1294. The enzymes used for site-specific conjugation covered in this review include formylglycine generating enzyme, sialyltransferases, phosphopantetheinyltransferases, O-GlcNAc post-translational modification, sortagging, transglutaminase, farnesyltransferase, biotin ligase, lipoic acid ligase, and N-myristoyltransferase.

Surprisingly, as shown throughout the examples section, the at least two analyte-specific binding agents, each bound to a single molecule of the second partner of the binding pair via a linker comprising from 12 to 30 ethylene glycol units (PEG 12 to 30), e.g., a monobiotinylated antibody, lead to very good assay performance, in particular with regard to assay sensitivity. This is very important in various diagnostics fields such as in the infectious disease area where infections must be reliably detected at early and later stages after infection.

In addition the use of at least two analyte-specific binding agents, each bound to the second partner of the binding pair, wherein said second partner of the binding pair is bound to each of said analyte-specific binding agents via a linker comprising from 12 to 30 ethylene glycol units (PEG 12 to 30), appears not to require mono-biotinylation or removal of conjugates of higher than 1:1 stoichiometry obtained by use of standard coupling chemistry. As expected, conjugate preparations comprising conjugates of higher than 1:1 stoichiometry tend to lead to bead aggregation. However, this effect is much less visible, pronounced if the second partner of the binding pair is bound to said analyte-specific binding agent via a linker comprising from 12 to 30 ethylene glycol units (PEG 12 to 30), even at higher than 1:1 stoichiometry.

A possible explanation might be that these relatively long and flexible PEG linkers allow for the rapid binding of many of the second partners of the binding pair to the binding sites of the first partner of such binding pair present and within reach on the coated microparticles. To the contrary, the several second partners of a binding pair on an analyte-specific binding agent may have too short linkers to bind to another first binding partner on the same microparticle and rather tend to find an appropriate first binding partner on a second microparticle—thereby obviously promoting a tendency for bead aggregation.

In order to avoid "over-labelling" with the second partner of the binding pair the up to now standard chemistry must use a relatively low ratio of the analyte-specific binding agent and the second member of the binding pair. In order to achieve a 1:1 stoichiometry of a conjugate preparation in average usually the second partner of the binding pair (e.g. biotin in a biotinylation reagent) is used in 1.3-fold excess over the analyte-specific binding agent (e.g. an antibody). At such 1.3 to 1 coupling conditions the resulting conjugate preparation comprises about 37% of non-conjugated antibody; about 37% of mono-biotinylated antibody, but also 18%, 6% and 2% of double-, triple- or more than triple-biotinylated antibody, respectively. Usually the fraction representing the 1:1-conjugate has to be purified for achieving optimal results in a commercial immuno assay.

To the contrary, if the second partner of the binding pair is bound to said analyte-specific binding agent via a linker comprising from 12 to 30 ethylene glycol units (PEG 12 to 30), standard coupling chemistry can be used—even with the to be coupled/bound second member of the binding pair at higher molar ratios—and not requiring the isolation of the fraction comprising the 1:1 conjugates. As obvious this, in addition to the performance of such conjugates in the methods disclosed herein, is a tremendous advantage in the production of such conjugates.

In one embodiment the present disclosure relates to a conjugated specific binding agent bound to the second partner of the binding pair comprised in a composition wherein in said composition the average molar ratio between the second partner of the binding pair bound to analyte-specific binding agent is 1.1 or more.

In one embodiment the present disclosure relates to a conjugated specific binding agent bound to the second partner of the binding pair comprised in a composition wherein in said composition the average molar ratio between the second partner of the binding pair bound to analyte-specific binding agent is between 1.1 and 10.

In one embodiment the present disclosure relates to a conjugated specific binding agent bound to the second partner of the binding pair comprised in a composition wherein in said composition the average molar ratio between the second partner of the binding pair bound to analyte-specific binding agent is between 1.2 and 6.

In one embodiment the present disclosure relates to a method for measurement of an analyte in a microparticle-based analyte-specific binding assay, wherein said microparticles are coated with the first partner of a binding pair, the method comprising a) mixing the coated microparticles, at least two analyte-specific binding agents, each bound to the second partner of the binding pair, and a sample suspected of comprising or comprising the analyte, wherein said second partner of the binding pair is bound to each of said analyte-specific binding agent via a linker comprising from 12 to 30 ethylene glycol units (PEG 12 to 30), thereby binding the analyte via the at least two analyte-specific binding agents to the coated microparticles and wherein said conjugated specific binding agents, each bound to the second partner of the binding pair are comprised in a composition wherein in said composition the average molar ratio between the second partner of the binding pair bound to analyte-specific binding agent is 1.1 or more, b) separating the microparticles comprising the analyte bound via the binding pair and the analyte-specific binding agents from the mixture and c) measuring the analyte bound to the microparticles.

In one embodiment the present invention relates to a kit comprising in separate containers or in separated compartments of a single container unit at least microparticles coated with a first partner of a binding pair and at least two analyte-specific binding agents, each bound to the second partner of said binding pair, wherein said second partner of the binding pair is bound to each of said analyte-specific binding agents via a linker comprising from 12 to 30 ethylene glycol units (PEG 12 to 30).

The term single container unit relates to the fact that for many automatic analyzers, like the Elecsys® analyzer series from Roche diagnostics, the reagents required to measure a certain analyte are provided in the form of a "reagent pack", i.e. as one container unit fitting on the analyzer and containing in different compartments all the key reagents required for measurement of the analyte of interest.

In one embodiment the present invention relates to a kit wherein said first partner of a binding pair is avidin or streptavidin, and wherein said second partner of said binding pair is selected from biotin or biotin analogues such as aminobiotin, iminobiotin or desthiobiotin.

In one embodiment the present disclosure relates to a kit comprising in separate containers or in separated compartments of a single container unit at least microparticles coated with avidin or streptavidin, and at least two biotinylated analyte-specific binding agents, wherein said biotin is bound to each of said analyte-specific binding agents via a linker comprising from 12 to 30 ethylene glycol units (PEG 12 to 30).

In an embodiment the invention concerns a kit as specified above, wherein said at least two analyte-specific binding agents are viral antigen-specific binding agents, in an embodiment viral antigen-specific antibodies. In yet another embodiment of the present invention one of said at least two viral antigen-specific binding agents is an antibody binding to an epitope within the amino acid positions 140 to 172 of SEQ ID NO:1, in an embodiment binding within amino acid positions 157-169 of SEQ ID NO:1 and one of said at least two viral antigen-specific binding agents is an antibody binding to an epitope within the amino acid positions 20 to 80, in an embodiment within the amino acid positions 65-71, in an embodiment within the amino acid positions 32-36, in an embodiment within the amino acid positions 37-46 of SEQ ID NO:1

In a further embodiment of the invention all embodiments of a kit additionally comprise a further analyte-specific binding agent which is detectably labeled. In another embodiment said labeled antibody binds to an epitope within amino acid positions 100-120 of SEQ ID NO:1.

The definitions and explanations made further above apply for all embodiments described in this specification mutatis mutandis.

Summarizing the findings of the present invention, the following embodiments are particularly envisaged:

1. A method for measurement of an analyte in a microparticle-based analyte-specific binding assay, wherein said microparticles are coated with the first partner of a binding pair, said method comprising
    a) mixing the coated microparticles, at least two analyte-specific binding agents, wherein each of said analyte-specific binding agents is bound to a second partner of the binding pair, and a sample suspected of comprising or comprising the analyte,
    wherein said second partner of the binding pair is bound to each of said analyte-specific binding agents via a linker comprising from 12 to 30 ethylene glycol units (PEG 12 to 30), thereby binding the analyte via the said analyte-specific binding agents to the coated microparticles,
    b) separating the microparticles comprising the analyte bound via the binding pair and the analyte-specific binding agent from the mixture and
    c) measuring the analyte bound to the microparticles.
2. The method according to embodiment 1, wherein said microparticles are from 50 nm to 20 μm in diameter.
3. The method according to embodiments 1 or 2, wherein said microparticles are paramagnetic and separation in step 1(b) is by magnetic forces.
4. The method according to any of claims 1 to 3, wherein said at least two analyte-specific binding agents are polypeptides of at least 50 amino acids.
5. The method according to any of claims 1 to 4, wherein said at least two analyte-specific binding agents are polypeptides of at most 10,000 amino acids.
6. The method according to any of claims 1 to 5, wherein said at least two analyte-specific binding agents are antibodies or antigen-binding fragments thereof.
7. The method according to any of embodiments 1 to 6, wherein said analyte is measured in a sandwich assay format.
8. The method according to any of embodiments 1 to 7, wherein said measuring of the analyte bound to the microparticles is based on use of an electrochemiluminescent label.
9. The method according to any of embodiments 1 to 8, wherein said first partner of the binding pair is selected from avidin and/or streptavidin, and FimG, respectively, and wherein said second partner of the binding pair is selected from biotin or biotin analogues such as aminobiotin, iminobiotin or desthiobiotin and DsF, respectively.
10. The method according to any of embodiments 1 to 9, wherein said first partner of the binding pair is avidin and/or streptavidin and wherein said second partner of the binding pair is biotin.
11. The method according to any of embodiments 1 to 10, wherein each of said analyte-specific binding agents each bound to the second partner of the binding pair is comprised in a composition wherein in said composition the average molar ratio between the second partner of the binding pair bound to analyte-specific binding agent is 1.1 or more.
12. The method according to any of embodiments 1 to 11, wherein said analyte comprises several variants.
13. The method according to any of embodiments 1 to 12, wherein said several variants are different genotypes, isoenzymes, isoforms, serotypes or mutants of said analyte.
14. The method according to any of embodiments 1 to 13, wherein said analyte is a peptide, a protein, a drug molecule, a hormone or a vitamin.
15. The method according any of embodiments 1 to 14, wherein each of said at least two analyte-specific-specific binding agents binds to an epitope of said analyte.
16. The method according to any of embodiments 1 to 15 wherein said epitopes are distinct epitopes.
17. The method according any of embodiments 1 to 16, wherein said analyte is an antigen of an infectious agent.
18. A method according any of embodiments 1 to 17, wherein said analyte is a viral antigen.
19. A method according to embodiment 18 wherein said analyte is a hepatitis virus antigen or a human retroviral antigen.
20. A method according to any of embodiments 18 to 19, wherein said analyte is a hepatitis C virus or a hepatitis B virus or an HIV antigen.
21. A method according to any of embodiments 19 to 20, wherein said analyte is hepatitis C virus core antigen.
22. The method according to embodiment 21, wherein one of said at least two analyte-specific binding agents is an antibody binding to an epitope within the amino acid positions 140 to 172, in an embodiment within amino acid positions 157-169 of SEQ ID NO:1 and one of said at least two analyte-specific binding agents is an antibody binding to an epitope within the amino acid positions 20 to 80, in an embodiment within the amino acid positions 65-71, in an embodiment within the amino acid positions 32-36, in an embodiment within the amino acid positions 37-46 of SEQ ID NO:1.
23. The method according any of embodiments 1 to 14, wherein said analyte is an antibody against an infectious agent.
24. A kit comprising in separate containers or in separated compartments of a single container unit at least microparticles coated with a first partner of a binding pair and at least two analyte-specific binding agents, bound to the second partner of said binding pair, wherein said second partner of the binding pair is bound to each of said analyte-specific binding agents via a linker comprising from 12 to 30 ethylene glycol units (PEG 12 to 30).
25. The kit of embodiment 24, wherein said first partner of a binding pair is avidin or streptavidin, and wherein said second partner of said binding pair is selected from biotin or biotin analogues such as aminobiotin, iminobiotin or desthiobiotin.
26. The kit according to any of embodiments 24 to 25, further comprising in a separate container or in a separated compartment of a single container unit a further analyte-specific binding agent which is detectably labeled.
27. The kit according to any of embodiments 24 to 26, wherein said at least two analyte-specific binding agents are viral antigen-specific binding agents, in an embodiment viral antigen-specific antibodies.
28. The kit according to any of embodiment 24 to 27, wherein one of said at least two analyte-specific binding agents is an antibody binding to an epitope within the amino acid positions 140 to 172, in an embodiment within amino acid positions 157-169 of SEQ ID NO:1 and one of said at least two analyte-specific binding agents is an antibody binding to an epitope within the amino acid positions 20 to 80, in an embodiment within the amino acid positions 65-71, in an embodiment within the amino acid positions 32-36, in an embodiment within the amino acid positions 37-46 of SEQ ID NO:1
29. The kit according to any of embodiments 26 to 28, wherein said further analyte-specific binding agent which is detectably labeled is an antibody binding to an epitope within amino acid positions 100-120 of SEQ ID NO:1.

The following examples and sequences are provided to aid the understanding of the present invention, the true scope of which is set forth in the appended claims. It is understood that modifications can be made in the procedures set forth without departing from the spirit of the invention.

Although the foregoing invention has been described in some detail by way of illustration and example for purposes of clarity of understanding, the descriptions and examples should not be construed as limiting the scope of the invention.

EXAMPLES

Example 1: Methods

Monoclonal Antibodies

Recombinant HCV core antigen needed for immunization of appropriate animals was obtained using standard techniques known in the art by inserting a DNA fragment encoding the desired antigen amino acid sequence into an *E. coli* expression plasmid followed by overexpression and purification of the protein. These standard molecular biological methods are described for example in Sambrook, J. et al., Molecular cloning: A laboratory manual; Cold Spring Harbor Laboratory Press, Cold Spring Harbor, N.Y., 1989.

Murine or rabbit monoclonal antibodies against HCV core were prepared by standard hybridoma technology or by recombinant nucleic acid techniques as known to the skilled person and in an analogous manner described e.g. in WO2016/091755, respectively.

Monoclonal antibodies against HCV core protein used as capture compounds in the examples below bind to the epitopes aa 157-169 or aa 32-36 or aa 37-46 or aa 65-71 of the HCV core protein (SEQ ID NO:1). Very similar epitopes and their determination have already been disclosed in EP1308507. As detection compound, a monoclonal antibody was chosen capable of binding to the core epitope aa 102-112, an epitope related to epitopes also described in EP0967484 and EP1308507. For the immunization of mice and rabbits, HCV core antigenic sequences of genotype 1a according to Genbank Acc. No: P26664.3 GI:130455 (SEQ ID NO:1), which discloses the complete polyprotein encoded by HCV genotype 1 were used.

In particular, peptides either from amino acid 110-171 as recombinant fusion protein with *Escherichia coli* SlyD following the procedure disclosed in WO 03/000878 A2, US 2009/0291892 A1, WO 2013/107633 A1 or peptides from amino acid 2-169 as recombinant protein following the procedure described by Boulant, S. et al., 2005, J. Virol. 79:11353-11365 were used for immunization. In an additional approach multiple peptides either from amino acid 82-117 or 9-48 coupled to KLH (keyhole limpet hemocyanin) were used for immunization according to known methods.

Protein Determination

The protein concentration of purified polypeptides was determined by determining the optical density (OD) at 280 nm, using the molar extinction coefficient calculated on the basis of the amino acid sequence of the polypeptide or using the colorimetric BCA method.

Example 2: Synthesis of Activated Biotinylation Reagents

The synthesis of state-of-the-art activated biotin-comprising linkers (biotinylation reagents) like the widely used linker Biotin-DDS is disclosed in EP 632 810.

Biotin-PEGn-NHS-biotinylation reagents (CAS-Nr. 365441-71-0; n=number of ethylene oxide units) were either obtained from IRIS Biotech GmbH or synthesized in house.

In the de novo synthesis the control of discrete number of ethylene oxide units was ensured by the stepwise elongation of shorter PEGs, such as tetraethylene glycol, following the described method from Chen and Baker, J. Org. Chem. 1999, 64, 6840-6873.

In a first step bis-trityl-$PEG_n$ 1 has been obtained (as obvious, n represents the number of ethylene glycol units).

Deprotection of 1 was carried out by stirring in 1M HCl in dioxane for 1 h at room temperature. After evaporation the residue was refluxed in methanol until a clear solution was obtained and the flask was kept at 4° C. overnight. After filtration the solution was extracted with hexane, the methanolic layer evaporated and dried to give the corresponding $PEG_n$-diol 2 as oil or wax (consistency depending on length/number of units (n) of the PEG).

Next the introduction of the acid function was carried out by sodium catalyzed addition of $PEG_n$-diol to tert-butyl acrylate according to Seitz and Kunz, J. Org. Chem. 1997, 62, 813-826. This way compound 3 is obtained.

To a solution of HO-$PEG_n$-COOtBu 3 (1 equivalent) and triethylamine (2.5 equivalents) in methylene chloride methylsulfonyl chloride (2 equivalents) was added drop-wise at 0° C. After stirring for 1 h aqueous work-up and evaporation followed.

The mesylate 4 (1 equivalent) was directly reacted with $NaN_3$ (2 equivalents) by stirring in dimethylformamide at room temperature for two days. After removal of the solids and dimethylformamide, aqueous work-up with diethylether and $Na_2CO_3$ followed.

The crude product 5 was purified by column chromatography on silica gel in ethyl acetate/methanol 15/1. Reduction of the azide 5 (1 equivalent) was performed by stirring for 24 h with triphenylphosphine (1.1 equivalents) in tetrahydrofurane/water 4/1 at room temperature. After evaporation the residue was suspended in water and washed with ethyl acetate several times. The water layer was evaporated and dried to give the amine 6 as colorless oil.

Cleavage of the tert-butyl ester was carried out with 5% trifluoroacetic acid in water. Amino-$PEG_n$-acid 7 was obtained by evaporation with water for several times.

Biotin was introduced by coupling with corresponding N-hydroxysuccinimide ester 8 (1.05 equivalents) with triethylamine (4 equivalents) in dimethylformamide at room temperature overnight.

After evaporation crude product 9 was purified by RP-HPLC in acetonitrile/water.

Finally, N-hydroxysuccinimide ester 10 was formed by reaction with N-hydroxysuccinimide (1.1 equivalents) and ethyl dimethylaminopropyl carbodiimide (1.1 equivalents) in methylene chloride. After completion of the reaction, the reaction mixture was diluted with methylene chloride and washed with water. Evaporation and drying led to pure Biotin-PEG$_n$-NHS 10 as oil, wax or solid, respectively depending on the number of ethylene oxide units.

Scheme 1

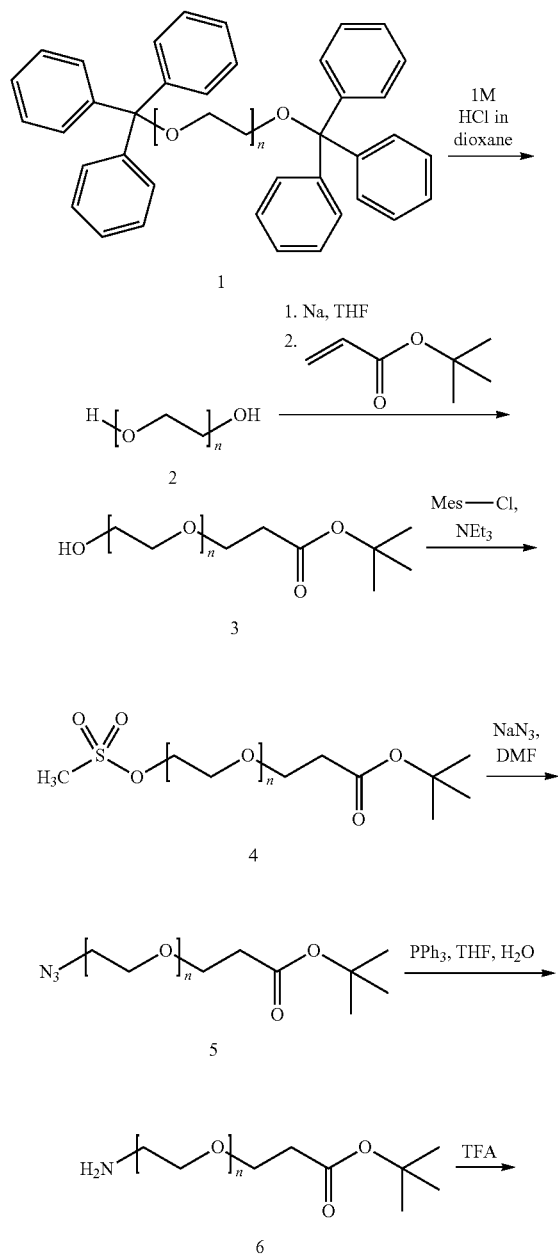

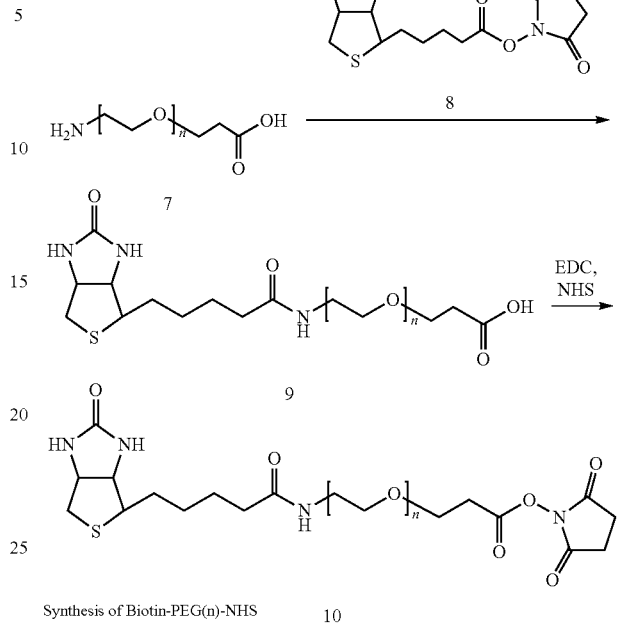

Synthesis of Biotin-PEG(n)-NHS 10

Example 3: Labeling of Antibodies

Coupling of biotin and ruthenium moieties, respectively, to antibodies:

Antibodies were obtained and purified according to state-of-the art procedures that are fully familiar to a person skilled in the art.

Prior to labeling, the detection antibody was cleaved by pepsin to obtain a F(ab')$_2$ fragment and to eliminate the interference prone Fc fragment (the method is described by A. Johnstone and R. Thorpe in Immunochemistry in Practice, Blackwell Scientific 1987). The purified F(ab')$_2$ fragment was further polymerized with the homobifunctional crosslinker disuccinimidyl suberate (DSS) and applied to a 5400 gel filtration chromatography to gather the optimal size range of the F(ab')$_2$ polymer (the principle is described in DE3640412).

For the attachment of the respective label, in general the lysine ε-amino groups of the antibodies were targeted by N-hydroxy-succinimide activated compounds. At a protein concentration of 10 mg/ml, antibodies were reacted with N-hydroxy-succinimide activated biotinylation reagents (Biotin-DDS or Biotin-PEG24-NHS) and N-hydroxy-succinimide activated ruthenium labeling reagents, respectively. The label/protein ratio of biotinylation or ruthenium labeling reagent was 5-6:1 or 15:1, respectively. The reaction buffer was 50 mM potassium phosphate (pH 8.5), 150 mM KCl. The reaction was carried out at room temperature for 15 minutes and stopped by adding L-lysine to a final concentration of 10 mM. To avoid hydrolytic inactivation of the labels, the respective stock solutions were prepared in dried DMSO (Sigma-Aldrich, Germany). After the coupling reaction, unreacted free biotin or ruthenium label was removed by passing the crude antibody conjugate through a gel filtration column (Superdex 200 HI Load) or by dialysis.

Example 4: Prototype Elecsys HCV Core Antigen Assay

Measurements of an Elecsys HCV core antigen prototype assay were carried out in a sandwich assay format on an automated Cobas® e601 analyzer (Roche Diagnostics GmbH). Signal detection in this analyzer is based on electrochemiluminescence. In this sandwich assay the one or more capture antibody-biotin-conjugates (i.e. analyte-specific binding agents) is/are immobilized on the surface of a streptavidin-coated magnetic bead. The detection-antibody (further analyte-specific binding agent) bears a complexed ruthenium cation as the signaling moiety. In the presence of analyte, the ruthenium complex is bridged to the solid phase and emits light at 620 nm after excitation at the platinum electrode comprised in the measuring cell of the analyzer. The signal output is in arbitrary light units. Measurements were performed with HCV core antigen positive and negative human serum and plasma samples purchased from several sources.

The experimental HCV core antigen assay was conducted as follows. 50 µl of normal human serum of HCV antigen positive sample and 25 µl of a detergent containing pretreatment reagent (PT: 0.25 M KOH, 1.125 M KCl, 1.5% hexadecyltrimethylammoniumchloride (HTAC), 0.75% octylglycoside) were incubated together for 9 minutes to release the antigen followed by the addition of 35 µl of 2 µg/ml of the respective capture antibody-biotin conjugate or a mixture of two different antibody-biotin conjugates (1 µg/ml each) and 40 µl of 1 µg/ml detection antibody ruthenium label conjugate in the same assay buffer R1 and R2 (200 mM potassium phosphate, pH 6.5, 225 mM KCl, 0.5% sodium taurodeoxycholate, 0.3% zwittergent 3-14, 0.1% oxypyrion, 0.01% methylisothiazolinone, 0.2% bovine serum albumin, 0.2% bovine IgG, 50 µg/ml MAK33-IgG1, 50 µg/ml MAK33-F(ab')$_2$-Poly, 50 µg/ml MAK IgG2b/Fab2a-Poly). After additional 9 minutes incubation time 50 µl streptavidin-coated paramagnetic microparticles were added and incubated for further 9 minutes. Afterwards, the HCV core antigen was detected (via the electrochemiluminescent signal generated in these experiments).

The data in Table 1 and 2 show the actual counts measured in HCV positive samples and in a normal (negative) sample, as well as the recovery relative to the reference for capture antibodies conjugated with the short biotin label Biotin-DDS (Table 1, state of art) and with the long biotin label Biotin-PEG24-NHS (Table 2, invention), respectively.

In this setup the cutoff (decision point above which a sample is regarded as reactive or positive and below which a sample is classified as non-reactive or negative) for all measurements was calculated as three times the signal of a negative (normal) sample in the same experimental setup. For example, if the background signal of a normal (negative) sample shows around 700 counts the cutoff is set at about 2100 counts. As a consequence, all samples showing more counts than 2100 are classified as reactive.

The capture antibody recognizing the HCV core antigen epitope aa 157-169 generates the highest specific signals and was chosen as reference. As can be seen from Table 2, by combining any other capture antibody with the reference antibody to a total concentration of 2 µg/ml (in R1) the signal level is very close to that generated by the reference antibody alone at 2 µg/ml as long as the long biotin label Biotin-PEG24-NHS is used according to the invention.

In contrast to this and as can be seen from Table 1, analogous mixtures of capture antibodies conjugated with the short biotin label Biotin-DDS known in the state of art exhibit a strong signal decline relative to the reference antibody used alone. The signal recovery relative to the reference is—depending on the respective antibody combinations—only around 40% or maximum 75%, whereas the recovery using the long linker biotin label according to the invention is at least 92%, mean values 91%, 95% and 96%, respectively (Table 2). This might indicate a stronger competition of biotinylated capture antibodies with the streptavin-coated solid phase conjugated with short biotin labels than for longer ones.

In order to assess the reliable recognition of different genotypes of HCV core antigen the prototype Elecsys HCV core antigen assay was performed using one or two capture antibodies conjugated with the long biotin label Biotin-PEG24-NHS. The antibody concentration of each antibody in R1 was further optimized for the mixture variant. Seroconversion panel of HCV genotype 1 and 3 were purchased from ZeptoMetrix Corporation. The data in Table 3 clearly exhibit the advantage of a mixture of capture antibodies over the single antibody variant. Using two antibodies binding to the HCV core antigen (invention) linked to the long biotin label Biotin-PEG24-NHS instead of one antibody, the signal increases for most seroconversion samples so that the assay reliably detects HCV genotype 1 and 3. The approach according to the current invention of using at least two analyte-specific binding agents conjugated to the long biotin label leads to a higher signal and thus to an improved sensitivity, in particular to an improved assay sensitivity for HCV core antigen detection.

TABLE 1

Prior art linker Biotin DDS for analyte-specific binding agents, HCV core antigen detection
Conjugation with Biotin-DDS

| HCV core antigen epitope of mAb | | (reference) 157-169 | | | | 157-169 | | 157-169 | | 157-169 | |
|---|---|---|---|---|---|---|---|---|---|---|---|
| | | | 65-71 | | | 65-71 | | | | | |
| | | | | 32-36 | | | | 32-36 | | | |
| | | | | | 37-46 | | | | | 37-46 | |
| concentration of mAb in R1 | | 2 µg/ml | 2 µg/ml | 2 µg/ml | 2 µg/ml | 1 µg/ml each | | 1 µg/ml each | | 1 µg/ml each | |
| | sample ID | counts | counts | counts | counts | counts | recovery relative to reference | counts | recovery relative to reference | counts | recovery relative to reference |
| normal sample | #960064560 | 1'019 | 660 | 956 | 516 | 856 | | 1'082 | | 630 | |
| HCV antigen positive samples | #217293 | 64'294 | 22'516 | 19'087 | 6'812 | 49'536 | 77% | 50'000 | 78% | 26'018 | 40% |
| | #205104 | 479'104 | 183'722 | 150'828 | 47'726 | 335'293 | 70% | 370'837 | 77% | 203'624 | 43% |
| | #205085 | 1'322'663 | 499'147 | 367'297 | 128'315 | 861'295 | 65% | 896'309 | 68% | 491'133 | 37% |

TABLE 1-continued

Prior art linker Biotin DDS for analyte-specific binding agents, HCV core antigen detection
Conjugation with Biotin-DDS

|      | #205081 | 68'063 | 28'008 | 26'054 | 8'910 | 53'318 | 78% | 54'913 | 81% | 29'032 | 43% |
|------|---------|--------|--------|--------|-------|--------|-----|--------|-----|--------|-----|
|      | #9174627 | 85'874 | 31'323 | 27'807 | 10'824 | 58'827 | 69% | 61'679 | 72% | 36'095 | 42% |
| mean |         |        |        |        |        |        | 72% |        | 75% |        | 41% |

TABLE 2

Long PEG linker (invention) for analyte-specific binding agents, HCV core antigen detection
Conjugation with Biotin-PEG24-NHS

| HCV core antigen epitope of mAb | (reference) 157-169 | | | | 157-169 | | 157-169 | | 157-169 | |
|---|---|---|---|---|---|---|---|---|---|---|
| | | 65-71 | | | 65-71 | | | | | |
| | | | 32-36 | | | | 32-36 | | | |
| | | | | 37-46 | | | | | 37-46 | |
| concentration of mAb in R1 | 2 µg/ml | 2 µg/ml | 2 µg/ml | 2 µg/ml | 1 µg/ml each | | 1 µg/ml each | | 1 µg/ml each | |

| | sample ID | counts | counts | counts | counts | counts | recovery relative to reference | counts | recovery relative to reference | counts | recovery relative to reference |
|---|---|---|---|---|---|---|---|---|---|---|---|
| normal sample | #960064560 | 1'080 | 1'103 | 970 | 960 | 1'083 | | 1'040 | | 1'143 | |
| HCV antigen positive samples | #217293 | 131'763 | 62'704 | 64'032 | 35'384 | 123'366 | 94% | 122'084 | 93% | 122'477 | 93% |
| | #205104 | 892'491 | 594'608 | 481'780 | 288'334 | 863'767 | 97% | 771'143 | 86% | 832'111 | 93% |
| | #205085 | 127'615 | 79'954 | 71'631 | 43'148 | 128'918 | 101% | 117'921 | 92% | 121'642 | 95% |
| | #205081 | 2'018'050 | 1'427'999 | 1'100'971 | 725'673 | 1'947'496 | 97% | 1'784'309 | 88% | 1'910'317 | 95% |
| | #9174627 | 139'911 | 77'536 | 81'413 | 57'186 | 128'076 | 92% | 132'503 | 95% | 137'170 | 98% |
| mean | | | | | | | 96% | | 91% | | 95% |

TABLE 3

HCV Seroconversion panels

| HCV core antigen epitope of mAb | 157-169 | 157-169 |
|---|---|---|
| | | 65-71 |
| concentration of mAb in R1 | 2 µg/ml | 1.25 µg/ml |
| | | 0.75 µg/ml |
| | counts | counts |
| normal sample #960064560 | 649 | 698 |

| seroconversion panel | HCV genotype | | |
|---|---|---|---|
| 10003_6 | 3 | 764 | 1'290 |
| 10003_7 | | 4'008 | 30'745 |
| 10003_11 | | 1'506 | 9'062 |
| 10003_12 | | 1'582 | 7'277 |
| 10010_1 | 1 | 5'321 | 3'876 |
| 10010_3 | | 904 | 1'296 |
| 10030_7 | 1 | 1'096 | 1'275 |
| 10030_8 | | 4'101 | 5'987 |
| 10032_4 | 3 | 720 | 954 |
| 10032_5 | | 1'293 | 11'724 |
| 10032_10 | | 853 | 3'189 |
| 10032_13 | | 797 | 2'992 |
| 10032_15 | | 755 | 2'221 |

The invention claimed is:

1. A method for measurement of an analyte in a microparticle-based analyte-specific binding assay, wherein said microparticles are coated with the first partner of a binding pair, said method comprising
   a) mixing the coated microparticles, at least two analyte-specific binding agents, wherein each of said analyte-specific binding agents is bound to a second partner of the binding pair, and a sample suspected of comprising or comprising the analyte, wherein said second partner of the binding pair is bound to each of said analyte-specific binding agents via a linker comprising from 12 to 30 ethylene glycol units (PEG 12 to 30), thereby binding the analyte via the said analyte-specific binding agents to the coated microparticles,
   b) separating the microparticles comprising the analyte bound via the binding pair and the analyte-specific binding agent from the mixture and
   c) measuring the analyte bound to the microparticles.

2. The method of claim 1, wherein said measuring of the analyte bound to the microparticles is based on use of an electrochemiluminescent label.

3. The method of claim 1, wherein said analyte comprises several variants.

4. The method of claim 1, wherein said several variants are different genotypes, isoenzymes, isoforms, serotypes or mutants of said analyte.

5. The method of claim 1, wherein said analyte is an antigen of an infectious agent.

6. The method of claim 1, wherein said analyte is a viral antigen.

7. The method of claim 1 wherein said analyte is a hepatitis virus antigen or a human retroviral antigen.

8. The method of claim 1, wherein said analyte is a hepatitis C virus or a hepatitis B virus or an HIV antigen.

9. The method of claim 1, wherein said analyte is hepatitis C virus core antigen.

10. The method of claim 1, wherein one of said at least two analyte-specific binding agents is an antibody binding to an epitope within the amino acid positions 140 to 172 of SEQ ID NO:1 and one of said at least two analyte-specific binding agents is an antibody binding to an epitope within the amino acid positions 20 to 80 of SEQ ID NO: 1.

11. A kit comprising in separate containers or in separated compartments of a single container unit at least microparticles coated with a first partner of a binding pair and at least two analyte-specific binding agents, each bound to the second partner of said binding pair, wherein said second partner of the binding pair is bound to each of said analyte-specific binding agents via a linker comprising from 12 to 30 ethylene glycol units (PEG 12 to 30).

12. The kit of claim 11, wherein said first partner of a binding pair is avidin or streptavidin, and wherein said second partner of said binding pair is selected from biotin or biotin analogues.

13. The kit of claim 11, wherein said at least two analyte-specific binding agents are viral antigen-specific binding agents.

14. The kit of claim 13 wherein one of said at least two viral antigen-specific binding agents is an antibody binding to an epitope within the amino acid positions 140 to 172 of SEQ ID NO:1.

15. The kit of claim 11, further comprising in a separate container or in a separated compartment of a single container unit a further analyte-specific binding agent which is detectably labeled wherein said further analyte-specific binding agent which is detectably labeled is an antibody binding to an epitope within amino acid positions 100-120 of SEQ ID NO:1.

* * * * *

SEQUENCE LISTING

<160> NUMBER OF SEQ ID NOS: 1

<210> SEQ ID NO 1
<211> LENGTH: 191
<212> TYPE: PRT
<213> ORGANISM: Hepatitis C virus

<400> SEQUENCE: 1

Met Ser Thr Asn Pro Lys Pro Gln Lys Lys Asn Lys Arg Asn Thr Asn
1               5                   10                  15

```
                            -continued

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
         50                  55                  60

Ile Pro Lys Ala Arg Arg Pro Glu Gly Arg Thr Trp Ala Gln Pro Gly
 65              70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
             115                 120                 125

Gly Phe Ala Asp Leu Met Gly Tyr Ile Pro Leu Val Gly Ala Pro Leu
         130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
             165                 170                 175

Phe Leu Leu Ala Leu Leu Ser Cys Leu Thr Val Pro Ala Ser Ala
                 180                 185                 190
```